United States Patent [19]
Yamanaka et al.

[11] Patent Number: 5,074,959
[45] Date of Patent: Dec. 24, 1991

[54] COMPLEX OF FIBERS AND FUNGI AND A PROCESS FOR PREPARATION THEREOF

[75] Inventors: Shigeru Yamanaka; Reiko Kikuchi, both of Kawasaki, Japan

[73] Assignee: Ajinomoto Company, Inc., Tokyo, Japan

[21] Appl. No.: 476,557

[22] Filed: Feb. 7, 1990

[30] Foreign Application Priority Data

Feb. 10, 1989 [JP] Japan .................................. 1-032180

[51] Int. Cl.⁵ .............................................. D21C 9/00
[52] U.S. Cl. ......................................... 162/9; 162/99; 162/145; 162/146; 162/148; 162/157.6
[58] Field of Search .................. 162/146, 157.6, 9, 13, 162/150, 176, 148, 91, 99, 145; 435/101, 179, 180, 911, 913, 929, 931, 939

[56] References Cited

U.S. PATENT DOCUMENTS 2,026,293 12/1935 Sanborn ............................. 162/158
2,811,442 10/1957 Van Horn et al. ................. 162/146
4,378,431 3/1983 Brown ................................. 435/101

FOREIGN PATENT DOCUMENTS 51-11902 1/1976 Japan ................................. 162/648
2165865 4/1986 United Kingdom .................. 162/91

OTHER PUBLICATIONS

Battista, *Synthetic Fibers in Papermaking*, (1964), Interscience Publishers, p. 5.
Casey, *Pulp and Paper*, 3rd ed., vol. II, (1980), John Wiley & Sons, p. 1163.
J82010240 Abstract (Japanese).
J5710280 Abstract (Japanese).

*Primary Examiner*—Peter Chin
*Attorney, Agent, or Firm*—Oblon, Spivak, McClelland, Maier & Neustadt

[57] ABSTRACT

A complex of fibrous material and fungi is prepared by allowing fungi to grow in a medium containing a fibrous material.

12 Claims, No Drawings

COMPLEX OF FIBERS AND FUNGI AND A PROCESS FOR PREPARATION THEREOF

BACKGROUND OF THE INVENTION

1. Field of the Invention

The present invention relates to a novel complex of fibrous materials and fungi obtained by allowing fungi to grow in a medium containing fibrous materials thereby bonding the fungi to the fibrous materials to the fungi.

The complex of fibrous material with fungi is utilized as building materials such as fiberboards, heat insulating materials, and the like; sound materials such as acoustic diaphragms, speaker cones, and the like; base materials for fiber-reinforced plastics (FRP); packing materials such as packages for floppy diskets, envelopes and the like; paper; and the like. As a result of employing the present process for preparing the complex, synthetic fibers containing the complex can be formed which exhibit a comfortable feeling. The present process is thus applicable to the fields of fibers and apparel.

2. Description of the Background

In order to prepare paper from pulp manufactured from wood, a beating step is necessary during the manufacturing process. That is, paper is formed by bonding pulp fibers to each other through hydrogen bonding, but the hydrogen bonding between pulp fibers is insufficient which means that it is impossible to obtain paper having a satisfactory strength from a practical viewpoint. Accordingly, pulp fibers are fibrilated during the beating step to increase the surface area. This results in enhanced hydrogen bonding between the fibers and therefore a practical paper product. However, exclusive facilities and large quantities of energy are required for such a beating step. No process is known for paper making which does not employ a pulp beating step.

Furthermore, in recent years there has been an increasing necessity of securing wood resources on a global scale. Conservation is aided by the recycling of waste paper, i.e., using the waste paper as a paper-making raw material. However, paper recycled from waste paper involves the problem that its strength deteriorates in comparison to paper prepared from pulp. That is, a portion of the fibers which constitute waste paper falls apart during the recycling step, thereby resulting in paper of diminished strength. Therefore, by mixing pulp prepared from wood with waste paper, waste paper can be better utilized.

An alternative to the use of waste paper and wood pulp as raw materials for paper making is a technique in which fungi are cultured in industrial waste water or city sewerage with pulp, as disclosed in (cf. Japanese Patent Publication No. 57-10280). However, the breaking length of paper prepared from the product of culturing is only less than 0.9 km and the strength of the paper is considerably weak in comparison to ordinary paper. Hence, such paper cannot be employed as a substitute for conventional paper.

British Patent Application Laid-Open No. 2,165,865, discloses a process in which fungi are treated with an alkali solution to expose chitin or chitosan, mixing the thus treated fungi, with other fibers to prepare non-woven fabric and using the non-woven fabric as wound dressings, wet wipes or adsorbents of metal ions. However, the non-woven fabrics prepared by the above process do not have a sufficient strength as paper, as is the case with the previously mentioned product prepared by mixing fungi with pulp.

In the manufacturing of fibers and apparel synthetic fibers such as polyester, nylon, and the like have been used. However, such fibers lack the comfortable feel associated with natural fibers such as cellulose, silk and the like. That is, these synthetic fibers readily generate static electricity since they do not adsorb moisture at all or they absorb only little moisture. Therefore, when one wears clothes prepared from such fabrics, the synthetic fibers give an uncomfortable feeling peculiar thereto, which is not realized in natural fibers. Further, synthetic fibers have no gloss in comparison to natural fibers because the surfaces of synthetic fibers are very smooth in comparison to the surfaces of natural fibers. In order to eliminate these problems, several attempts have been made to mix synthetic fibers and natural fibers or to artificially generate unevenness on the surface of synthetic fibers. Even with these treatments, however, it is not possible to prepare synthetic fibers or fabrics which have a touch comparable to silk among natural fibers. A need therefore continues to exist for a substitute for material fibers.

SUMMARY OF THE INVENTION

Accordingly, one object of the present invention is to prepare a paper which has a strength comparable to that of paper prepared in a conventional manner, by a process which does not require a beating step and further which improves upon the strength of paper recycled from waste paper to increase the utilization rate of waste paper.

Another object of the invention is to impart a silky touch to synthetic fibers.

Briefly, these objects and other objects of the present invention as hereinafter will become more readily apparent can be attained in a process for preparing a complex of fungi and fibrous material by growing fungi in a medium containing a fibrous material.

DETAILED DESCRIPTION OF THE PREFERRED EMBODIMENTS

As a result of investigations directed to solving the problems described above, it has been found that a complex of a fibrous material and fungi can be obtained by allowing fungi to grow in a medium containing a fibrous material and that this complex exhibits excellent strength. The complex can enhance the utilization rate of waste paper when waste paper is recycled.

The fibrous material employed in the present invention is selected from a variety of materials including pulp such as softwood pulp, hardwood pulp, synthetic pulp, or a mixture thereof; cotton fiber; disintegrated waste paper; synthetic fibers such as polyester, nylon, polyethylene, and the like; inorganic fibers such as alumina, carbon fibers, and the like; all other fibrous materials or sheet-like fabrics of these fibers or slurries of these fibers.

The fungi employed in the process include fungi belonging to the genus Aspergillus, the genus Mucor, the genus Rhizopus, the genus Fusarium, the genus Saprolegnia, and the like.

As a medium for culturing of the fungi, a medium containing organic and inorganic nutrients is employed. The medium is added to the aforesaid fibers, as they are, or to a slurry of the fibers, where the fiber content ranges from 0.05 to 80%. The concentration of organic nutrients in the medium may be as small as 1/10 to 1/100 of the organic nutrient content of ordinary culture media. The cultivation method may be either a static culture or an agitated culture. When the medium is agitated, the medium should be gently agitated such that the fungi does not solidify into a pellet. Culturing may be carried out at a temperature of 5° C. to 65° C. for a time period of 0.5 to 10 days. When culturing is performed under the conditions described above, a large number of hyphae grow from the surface of the fibers. Thus, the complex of fibrous material and fungi can be obtained.

When preparing paper from this complex as a raw material, no beating step is required. The thus prepared paper has a sufficient strength in comparison to conventional paper. Of course in the manufacture of ordinary paper, pulp fibers which have been beaten are employed. In this case, the isolated fibrils from the surface of native pulp enhance the bonding strength of the fibrilated pulp fibers so that a strengthened paper can be obtained. On the other hand, when the complex of fibers and fungi obtained by the process of the present invention is subjected to paper-making, the fungi which have grown on the surface of the fibers mediates the bonding so that it is possible to obtain paper having a strength no less than that of ordinary paper prepared from fibrilated pulp fibers.

In preparing paper using waste paper as a raw material, hyphae of the fungi are grown on the pulp fibers by applying the technique of the present invention. By doing so, paper having a sufficient strength can be prepared using waste paper alone as a raw material for paper-making. Of course the complex of the present invention is used together with the ordinary prepared pulp as a raw material.

When culturing is carried out using threads or clothes of synthetic fibers such as polyester or nylon, hyphae grow on the surface of the synthetic fibers as described above. The hyphae have a high water absorptability so that the complex having a good silky touch can be obtained.

A characteristic of the present process is that hyphae grow from the surface of the fibers by culturing fungi in the presence of the fibers. When culturing is initiated, it is thought that the edge of hyphae bind to the surface by any action and start growing. Consequently, fibers to which a large number of hyphae are bound have a branch like structure. While it is currently unclear as to what the bonding mechanism is between the hyphae edge and the fiber surface, it is thought that the hyphae would decompose a portion of the fibers to form holes or cracks therein into which hyphase would penetrate. Even though the complex obtained by bonding hyphae to fibers is placed in water and agitated, it is not easy to separate the hyphae and the fibers. Since one end of the hyphae is bound to the fibers as such, a sheet having a high strength can be obtained when the thus obtained complex is subjected to paper-making. In this regard, if fungi alone are separately cultured and then mixed with fibers, the bonding between the fibers and the hyphae, which forms when fungi are cultured in the presence of the fibers as achieved in the present invention, does not occur. Therefore, the strength of a sheet obtained by subjecting a mere mixture of hyphae and fibers to paper-making is lower than the strength of a sheet obtained from a complex of hyphae and fibers prepared by culturing fungi in the presence of fibers.

As described above, hyphae are allowed to grow on the surface of various fibrous materials to obtain the complex. When the final product is contaminated with components of fungi such as pigments, proteins, and the like, which are inconvenient, these components may be removed or decomposed after completion of the culturing by washing the complex with an acid solution, an alkali solution, a surface active agent, an organic solvent, or the like, or by bleaching.

Having now generally described this invention, a further understanding can be obtained by reference to certain specific examples which are provided herein for purposes of illustration only and are not intended to be limiting unless otherwise specified.

EXAMPLE 1

Medium I

| | |
|---|---|
| Hardwood pulp | 2.0 g |
| Yeast extract (Difco Co.) | 0.3 g |
| Malt extract (Difco Co.) | 0.3 g |
| Polypeptone (Daigo Co.) | 0.5 g |
| Glucose | 1.0 g |
| Tap water | to make 1 liter |

(1 liter each was separately charged in a shaker flask of 3 liter volume)
pH = 7.0, autoclaved at 120° C. for 20 minutes.

The pulp was disintegrated in a disintegrator (manufactured by Kumagai Riki Industry Co., Ltd.). Conditions for disintegration were room temperature, 3,000 rpm for 3 minutes in the medium.

Medium II

| | |
|---|---|
| Potato dextrose agar (Nissui Pharmaceutical Co., Ltd.) | 39 g |
| Tap water | to make 1 liter |

(150 ml each was separately charged into a Roux flask of 500 ml volume)
pH 5.6 ± 0.1, autoclaved at 120° C. for 20 minutes.

The fungus (*Aspergillus oryzae* ATCC 15240) was cultured in medium II at 28° C., for 3 to 4 days. The cells were thoroughly suspended by adding thereto 30 ml of 0.9% saline per one Roux flask. The cells were passed through sterilized cotton to obtain spores alone. The spore suspension was stored at −80° C. Each shaker flask employed filled with medium I was inoculated with 1 ml each of spore suspension. While gently stirring at 60 rpm with a magnetic stirrer, culturing was conducted at 28° C. for 2 days. Water and spores were removed from the culture solutions by sieving through a 200 mesh sieve. Further by repeated washing with distilled water, pure white hyphae-containing pulp was obtained. The obtained hyphae-containing pulp was suction filtered to eliminate a heterogeneous product and the filtered product was formed into a sheet. The sheet was dried at 105° C. to a constant weight and hot-pressed to give a sheet having a uniform thickness.

For a control, a sheet was prepared from a mixture of pulp and fungi grown on pulp-free medium I and sheets made of pulp alone (two kinds of sheets; prepared from a process employing a beating step and another prepared by a process not employing a beating step) were used. In each case, disintegration of the pulp, autoclaving and sheeting were performed under the same conditions described above.

The breaking length, folding endurance and dimensional stability of the sheets prepared were examined.

The dimensional stability of each sheet was determined by drawing a line on a sheet, wetting the sheet with water, then drying and determining the ratio of the length of the line drawn on the thus treated sheet to the original length. The results are shown in Table 1.

TABLE 1

| Sample Sheet | Breaking Length (km) | Folding Endurance (time) | Dimensional Stability (%) |
|---|---|---|---|
| Hyphae were cultured in the presence of pulp. | 5.78 | 1213 | 95 |
| After culturing hyphae, pulp was mixed with hyphae. | 3.25 | 556 | 88 |
| Pulp alone, no beating | 1.98 | 45 | 7 |
| Pulp alone, with beating | 5.86 | 1009 | 97 |

From the above results, it should be evident that when fungi were cultured in the medium containing pulp, the strength of the paper product prepared therefrom was approximately 2.2 times that of the paper prepared from pulp alone which was not beaten and approximately 1.7 times the strength of a paper prepared from a mere mixture of hyphae and pulp. The strength of the sheet of the present invention was comparable to that prepared from pulp alone which had not been beaten.

EXAMPLE 2

Medium III

| Yeast extract | 1.5 g |
|---|---|
| Malt extract | 1.5 g |
| Polypeptone | 2.5 g |
| Glucose | 1.0 g |
| Tap water | to make 1 liter | pH = 7.0, thermally sterilized at 120° C. for 20 minutes.

Medium I was sprayed onto autoclaved hardwood pulp and a spore suspension of *Aspergillus sojae* ATCC 20245 was inoculated thereon followed by culturing at 28° C. for 2 days. After culturing, the cells were washed with tap water on a sieve of 200 mesh and then autoclaved at 120° C. for 20 minutes. The obtained pulp-hyphae mixture was formed into a web. The web was drawn, adhered, dried and wound up on a conveyor belt to prepare a sheet.

For controls, a sheet prepared from pulp alone and a sheet prepared from a mixture of pulp and hyphae in amounts equal to those described above were prepared.

The basis weight, breaking length and folding endurance of the thus prepared sheets and conventional dust paper were examined.

The results are shown in Table 2.

TABLE 2

| Fibrous Material | Hyphae was cultured in the presence of pulp | After culturing hyphae, pulp was mixed hyphae. | Pulp alone, no beating | Dust Paper |
|---|---|---|---|---|
| Basis wt. (g/m²) | 70 | 70 | 72 | 71 |
| Breaking length (km) | 7.58 | 6.84 | 2.43 | 7.86 |
| Folding endurance (time) | 2630 | 980 | 58 | 1035 |

From the above results, it is clear that by culturing fungi on pulp, a clean wiper having excellent breaking length and folding endurance was obtained.

EXAMPLE 3

| Polyester woven cloth | 5.0 g |
|---|---|
| Yeast extract | 0.3 g |
| Malt extract | 0.3 g |
| Polypeptone | 0.5 g |
| Glucose | 1.0 g |
| Tap water | to make 1 liter | pH = 7.0

Culturing was carried out in a manner similar to Example 2 to give sheets made of polyester fibers and hyphae. Using these sheets, organoleptic tests on touch were performed. The results are shown below. For purposes of comparison, a woven cloth of polyester fibers and a silk woven cloth were used. The results are shown in Table 3.

TABLE 3

| Evaluation | Complex of Fungi/Fibrous Material (personnel) | Polyester (personnel) | Silk (personnel) |
|---|---|---|---|
| Good | 20 | 9 | 23 |
| Medium | 6 | 9 | 4 |
| Bad | 3 | 11 | 2 |

The results above show that a comfortable feeling can be imparted to polyester by culturing fungi in the presence of polyester.

EXAMPLE 4

Waste newspaper was cut into 1×3 cm pieces and 3 g of the resulting pieces were mixed with 1000 ml of water together with 0.2 g of sodium hydroxide and 0.5 g of sodium silicate. After an addition of sodium hypochlorite to the mixture in an amount of available chlorine of 0.02%, the mixture was disintegrated with a disintegrator (manufactured by Kumagai Riki Industry Co., Ltd.). Conditions for the disintegration were room temperature at 3000 rpm for 20 minutes. The resulting disintegrated solution was concentrated to a solids content of 7% by a suction filtration. The concentrate was resuspended in 1000 ml of water and the suspension was neutralized with hydrochloric acid. The suspension was again concentrated to a solids content of 7% by suction filtration and 1000 ml of water was further added to the concentrate to give a pulp slurry.

Medium components were added to 1000 ml of this pulp slurry in final concentrations of 30 g/l of yeast extract, 30 g/l of malt extract, 50 g/l of polypeptone and 100 g/l of glucose, pH 7.0 (adjusted with hydrochloric acid and sodium hydroxide). Then, the pulp slurry was inoculated with 1×10⁴/ml of *Aspergillus sojae* ATCC 20245 spores. By culturing at 28° C. for 3 days with gentle agitation, a slurry was obtained (culture slurry).

Next, the medium composed of 30 g of yeast extract, 30 g of malt extract, 50 g of polypeptone and 100 g of glucose, 1.0 liter of tap water; adjusted to pH 7.0, in the same concentration was inoculated with the same fungi. By culturing at 28° C. for 3 days with gentle agitation, hyphae were obtained. The hyphae were mixed with the concentrate obtained by concentrating the aforesaid pulp slurry obtained by disintegration of 30 g of conventional newspaper to a concentration of 7% with agitation thereby obtaining a slurry (slurry mixture).

The aforesaid 3 kinds of slurry, culture slurry, slurry mixture and pulp slurry were each filtered through an 80 mesh sieve having a diameter of 16 cm and further washed twice with 1 liter of hot water at 55° C. The resulting filtrates were squeezed out under pressure to form wet mats. The mats were dried under applied tension to give sheets. The properties of the 3 sheets were examined. The results are shown in Table 4.

TABLE 4

| Kind of Sheet | Breaking Length (km) |
| --- | --- |
| Sheet prepared from culture slurry | 2.54 |
| Sheet prepared from slurry mixture | 1.66 |
| Sheet prepared from pulp slurry | 1.21 |
| Recovered used newspaper | 2.25 |

The sheet prepared from the pulp slurry and the sheet prepared from the slurry mixture of fungi hyphae and pulp slurry cannot be used as raw materials for making newspaper since the breaking lengths thereof were quite poor in comparison to the breaking lengths of the newspaper. However, the sheet prepared from the culture slurry obtained by culturing fungi and pulp slurry at the same time can be re-used as newspaper since the sheet obtained is stronger than the sheet of newspaper.

EXAMPLE 5

The 3 kinds of sheets prepared in Example 4 were each cut up into 1×3 cm pieces, and the resulting pieces were disintegrated in the manner described above. Sheets were prepared from each of the three slurries obtained by disintegration and the breaking lengths were measured. The sheets were again cut and disintegrated to form sheets and the breaking lengths were measured. This operation was repeated 3 times and the three measurement values of the breaking length in total were obtained for each sheet. The results are shown in Table 5.

TABLE 5

| Kind of Sheet | Breaking Length (km) | | | |
| --- | --- | --- | --- | --- |
| (Sheet prepared in Example 4) | 0*1 | 1st*1 | 2nd*1 | 3rd*1 |
| Sheet prepared from culture slurry | 2.54*2 | 2.49 | 2.30 | 2.28 |
| Sheet prepared from slurry mixture | 1.66*2 | 1.16 | 0.99 | 0.75 |
| Sheet prepared from pulp slurry | 1.21*2 | 0.95 | 0.88 | 0.73 |

*1: Number of times of sheet regeneration . . .
*2: Breaking length in Example 4.

When disintegration and paper-making are repeated using as raw materials the sheet prepared from the pulp slurry or the sheet prepared from the slurry mixture of fungi hyphae and pulp slurry, the breaking length of the sheets are rapidly reduced by repeated disintegration and paper-making. To the contrary, when disintegration and paper-making are repeated, using as raw materials the sheet prepared from the culture slurry obtained by culturing fungi and pulp slurry together, the breaking length of the sheet was not reduced appreciably.

By implementing the process of the present invention, paper having a high strength can be prepared without requiring any beating step, in the paper-making industry. Furthermore, in the instances where waste paper is used as raw material for paper-making, paper having a sufficient strength can be prepared from waste paper alone, resulting in appreciable savings of raw materials for paper-making, thus contributing to the conservation of natural wood resources. In the fiber industry, when hyphae of the fungi are grown on synthetic fibers such as polyester fiber, and the like, a silky touch is imparted to the fibers.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing a complex of a fibrous substrate and fungi, comprising:
   growing fungi in an aqueous medium containing a fibrous substrate selected from the group consisting of natural and synthetics fibers;
   wherein said fungus growth is sufficient to produce hyphae growth on the surface of said fiber substrate and sufficient to increase the hydrophilicity or strength of said fiber substrate; and
   recovering said complex of said fibrous substrate and fungi.

2. The process of claim 1, wherein said fibrous substrate is pulp.

3. The process of claim 1, wherein said fibrous substrate is selected from the group consisting of cotton, carbon fibers, and inorganic fibers.

4. The process of claim 1, wherein said fungi is selected from the genus consisting of Aspergillus, Mucor, Rhezopus, Fusarium and Saprolegnea.

5. The process of claim 4, wherein said fungi belongs to the genus Aspergillus.

6. A process for preparing paper, comprising:
   preparing a complex of pulp and fungi by growing fungi in an aqueous medium containing pulp or paper;
   wherein said fungi growth is sufficient to produce hyphae growth on the surface of said pulp or paper; and
   preparing paper from said complex or a pulp mixture containing said complex.

7. The process of claim 6, wherein a portion of said pulp is selected from the group consisting of soft wood pulp, hard wood pulp, and disintegrated waste paper, cotton and used paper.

8. The process of claim 6, wherein in making paper from said complex of said pulp mixture a step in which said complex of said mixture is beaten, is not employed.

9. A complex of a fibrous substrate and fungi prepared by a process comprising:
   growing fungi in an aqueous medium containing a fibrous substrate selected from the group consisting of natural and synthetic fibers;
   wherein said fungi growth is sufficient to produce hyphae growth on the surface of said fiber substrate and sufficient to increase the hydrophilicity or strength of said fiber substrate.

10. The complex of claim 9, wherein said fungi is selected from the genus consisting of Aspergillus, Mucor, Rhezopus, Fusarium and Saprolegnea.

11. The complex of claim 9, wherein said fungi belongs to the genus Aspergillus.

12. The paper of claim 6.

* * * * *